US00PP09733P

United States Patent [19]

Rothberg

[11] Patent Number: Plant 9,733

[45] Date of Patent: Dec. 3, 1996

[54] ELEPHANT GRASS DENOMINATED "PROMOR A"

[76] Inventor: Morton S. Rothberg, 2536 Barstow Ave., Clovis, Calif. 93611

[21] Appl. No.: 357,644

[22] Filed: Dec. 16, 1994

[51] Int. Cl.[6] ..... A01H 5/00

[52] U.S. Cl. ..... Plt./100

[58] Field of Search ..... Plt./100

*Primary Examiner*—James R. Feyrer

*Attorney, Agent, or Firm*—Worrel & Worrel

[57] ABSTRACT

A new and distinct variety of elephant grass which possesses the unique and distinctive characteristic, when compared with other varieties of elephant grass, of a stooling, or tillering, ability, and which produces exceptionally high yields with very high nutritional values, particularly of protein, and which is otherwise excellently suited to a variety of usages including usage as a forage grass.

1 Drawing Sheet

BACKGROUND OF THE NEW VARIETY

The present invention relates to a new and distinct variety of elephant grass and, more particularly, to an elephant grass, hereinafter denominated "Promor A", which is excellently suited for use as a forage grass in that it produces an extremely high yield and possesses very high nutritional values.

Different varieties of grasses have been developed and otherwise adapted for usage in achieving a diverse assortment of tasks. For example, certain varieties of grasses have been found well suited to uses in landscaping, for erosion control and as forage for domesticated and undomesticated animals. The suitability of the grass varieties to particular uses is, of course, influenced by their adaptability to a wide variety of environmental considerations such as climate, soil conditions and the like.

Where forage usages are concerned, there is a multiplicity of concerns not experienced with other usages. For example, in forage usages the nutrient value of the grass variety is a prime concern as well as the accessibility of the available nutrients to the animals through digestion. Available proteins are of particular importance. The suitability of the raw grass fibers to intermixing with admixtures of other components and supplements in the formation of a processed feed is a consideration, as well as the palatability of the resulting product. Drought tolerance, resistivity to pests, adaptability to different types of soils, elevations and temperature ranges are also significant considerations. The elephant grass of the present invention appears to be uniquely well suited to this area of usage as well as to other areas of usage.

ORIGIN AND ASEXUAL REPRODUCTION OF THE NEW VARIETY

The variety of elephant grass hereof was discovered by the inventor in 1987 in the city of Feira de Santana, State of Bahia, Brazil, in a field of cultivated elephant grass with mixed clones of the species *Pennisetum purpureum*. The new variety was discovered during a search for forage grasses suitable for use as a ration component for feed particularly to be employed in the fattening of cattle.

The new variety was first asexually reproduced by the inventor in Brazil in a field of cultivated elephant grass located on a farm near the district of Jacu, Teodoro Sampaio, State of Bahia. The asexually reproduced plants were observed thereafter and found to be identical in every respect to the parent plants.

The subject variety was subsequently asexually reproduced on a farm in a rural district near Feira De Santana, Bahia, Brazil. These asexually reproduced plants were also observed through the following years and again confirmed to be identical in every respect to the parent plants except for the predicatble influences of the differences in climate in the respective growing areas.

The new variety was asexually reproduced in the San Joaquin valley near Kingsburg, Calif., in the United States of America in 1994 where it is now being tested for mass yield and nutritional qualities. The planting is in a fertile sandy loam soil with a Ph of over 7 and is irrigated by a furrow system. The new variety in this planting is identical in all botanical respects to the parent plants.

SUMMARY OF THE NEW VARIETY

The new variety of the present invention is exceptionally high in protein content and is excellently sited to blending in a feed ration as a valuable source of amino acids. The variety has demonstrated salt tolerance and is outstanding for its various agronomic characeristics including, exceptionally high mass yields, dense tillering with newly ratooned stools exhibiting very high individual shoot counts, early closing in and consequent competitiveness against weeds, resistance to periods of drought and high overall nutritional values.

DETAILED DESCRIPTION OF THE NEW VARIETY

Figure 1:
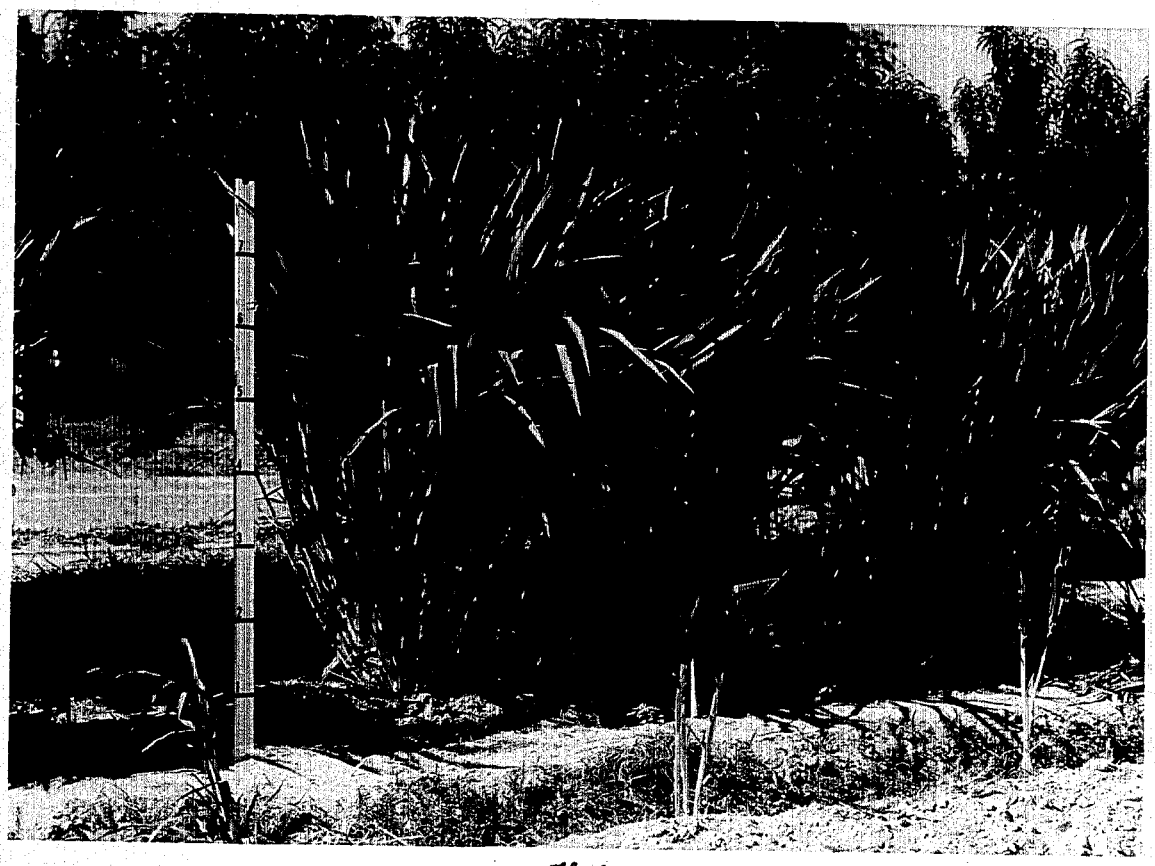
FIG. 1 is a photograph depicting a stand of the elephant grass variety of the present invention in situ with a measuring instrument demarcated in feet oriented in upstanding relation to illustrate the size of the new variety.
Figure 2:
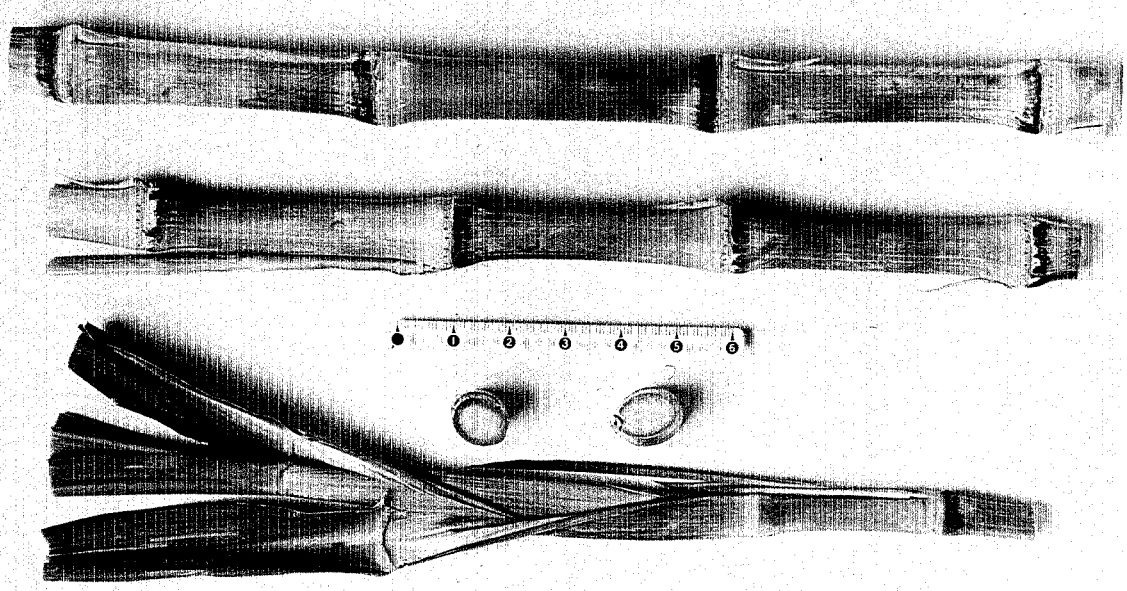
FIG. 2 is a photograph showing three stalk sections of the new variety in side elevation and two stalks in cross section through the internodes thereof together with a measuring instrument demarcated in inches and fractions thereof.

Referring more specifically to the botanical details of this new and distinct variety of elephant grass, the following has been observed under the ecological conditions prevailing near Kingsburg, Calif. in the United States of America. All major color code designations are by reference to the Maerz and Paul, *Dictionary of Color*, First Edition. Occasionally general color designations are employed.

Field Tests Of The New Variety

The new variety was asexually reproduced and tested for its nutritional content and mass yield along with other varieties of elephant grass for purposes of comparison. Initial testing was carried out on tertiary phase soils associated with the former Atlantic Coast Forest tablelands in Brazil. These kaolonitic soils are noted for a sandy siliceous topsoil and an increasing quantity of yellowish to red clay in the subsoil. The soils are acidic wih a Ph ranging from 4.5 to 5.5 and are quite infertile. Rainfall in the area ranges from 1200 to 1500 millimeters per year. In a normal year, there are two distinct wet and dry seasons.

During the tests, the new variety was observed to possess outstanding agronomic characteristics in numerous respects. Most notably, the new variety had an exceptionally high mass yield of over 300 tons per hectare year. Dense tillering with newly ratooned stools exhibited very high individual shoot counts. The variety exhibied an early closing in and consequent competitiveness against weeds, resistance to periods of drought and high nutritional values. In the tests, leaf blade heights reached one meter in approximately four weeks and tiller counts averaged between 45 to 60 stalks. Plantings were on a 0.80 meter row spacing and stool counts were averaging two per lineal meter. Tillering counts increased in the first few ratoons over the first harvest as the stools increased in size and number of culms.

In a manner similar to sugarcane, the roots of the grass from previously harvested culms support and nourish the stool until the roots of the new culms initiate elongation. This is the reason for the very rapid re-growth of recently harvested stools. Rooting is very prolific and preliminary observations indicated a dense rooting pattern with lateral and vertical root development at least 1.5 meter from the center of the stool. As the old roots die and decay after each harvest, a very significant mass of organic matter is formed; and for this reason, the grass has the characteristics of being able to improve marginal soils. This improvement was apparent in the infertile, acidic, former Atlantic Coast Forest tablelands of Brazil where the A horizon increased in depth and the B horizon demonstrated an increased fertility and organic matter content.

Protein content in the subject variety was consistently over 15% in the tests and at least 5% to 6% more than the other varieties of Pennisetum. Nitrogen was applied in amounts ranging from 80 to 150 units per acre together with phosphorous and potassium to all of the varieties. Mass yields of this close averaged approximately 30% to 40% over other varieties.

The subject grass variety was also planted and spread in an extremely heavy and fertile montmorillonitic soil underlain with a maritime limestone deposit and a Ph varing from 7.5 to 8.5. The grass exhibited the same exceptional growing characteristics in this soil and its protein content was consistent with the kaolonitic soil test area. The grass from this planting was fed to sheep and a mixed breed Brahman dairy cow herd with excellent results. The sheep preferred the instant new variety of grass over other species of grasses, such as various varieties of Brachiaria. It was observed that the fertility of the sheep herd appeared ti increase.

Feeding tests were conducted with the subject grass using the California Net Energy System as the method for balancing the ration components. Seven lots were selected for this test; five lots of ten bulls of mixed Brahman of the Nelore and Idubrasil sub-races, one lot of ten mixed Brahman×Holstein bulls, and one lot of older heavier bulls of mixed Brahmam origin. The green chopped grass component averaged approximately 25% by weight of the total ration given daily to the animals. The other two main components of the ration were tropical fruit pulp including, pineapple, papaya, passion fruit, acerola, cashew, and citrus as the carbohydrate source; and the tropical legume Leucaena Leucocephala cv. Cunningham. Small amounts of passion fruit seed and urea were also used to test for tolerance to these protein sources. A complete mineral salt was fed to the animals by mixing into the ration components. The test lasted 120 days. The first group of five lots gained from 1.10 to 1.28 kilos per day; the older initially heavier lot gained 1.23 kilos per day; and the mixed Brahman×Holstein group gained 1.69 kilos per day. The balanced ration was accepted by the animals from the start of the experiment and no digestive, or any other problem, was observed. Weight gains were considered to be excellent and the balanced ration was cost effective in this situation. The green chopped grass was also administrated to horses in an adjoining corral to verify palatability and acceptance. The horses accepted the grass with no problems and the green chop was continued for the same 120 day period with the animals remaining in excellent condition.

Another feeding test using two lots of bulls which were highly selected for desirable characteristics for feed lot trials was conducted. The two lots consisted of ten animals each. The first lot was made up of pure Nelore Brahman and the second lot consisted of a mixed Nelore Brahman×Chianina. This test was similar to the above-mentioned trial except than another variety of Pennisetum was used which was inferior in its nutritional qualities compared to the clone of the subject invention. Both lots gained an average of 0.8 kilos per day over the 120 day period.

An experiment was also carried out to test the subject grass for its composting characteristics. The grass was grown to a height of over five meters to increase its fiber and carbon content and then green chopped and laid out in an adjoining field in layers of approximately 0.40 meters high. The individual layers of grass were inoculated with raw manure from the test animals and a 20% super phosphate fertilizer was very lightly applied to the manure. Additional layers were added using the same constituents until the pile reached a height of over two meters. Moisture was maintained at fifty percent and the pile turned at 15 days with a front end loader. Thereafter, the pile was mixed every seven days to ensure adequate aeration and the process terminated at 120 days when a very homogeneous compost had been formed. Laboratory analysis confirmed that the resulting compost had an excellent carbon to nitrogen ratio. The compost was applied to the fruit trees from which pulp had been used to make the original ration for the feeding trials. This experiment demonstrated that the grass of the subject invention can provide an extremely high biomass weight to make microbe specific composts.

The grass was cut and chopped in the above experiment with a very simple one line forage harvester attached to the three point hitch of a 70 HP tractor and run off the power take off. Time and motion studies indicated that up to 35 metric tons per hour could be harvested in flat culture with 200 meter lengths of block. This operation demonstrated the ease with which the grass of the subject invention can be harvested.

The subject grass has also been planted, as previously noted, in the San Joaquin Valley near Kingsburg, Calif., where it is being multiplied asexually and tested for mass yield and nutritional qualities. This planting is in a fertile sandy loam soil with a Ph of over 7 and is irrigated by a furrow system. In this planting, a pair of four month old stools of the new variety planted on a spacing of 1.5 by 1.5 meters and selected as being average were harvested for measurement. The following data was produced from such measurement: average stalks per stool—115.5; average weight per stool—33.2 kilograms; and average weight per stalk 0.287 kilograms. Extrapolating this data to an area of one hectare, the yield of the four month old stools was computed to be 147.56 metric tons/hectare (65.71 short tons/acre). Based on the nutritional analysis of a composite sample taken at that time, the dry matter of the sampled stools was approximately 15.50%.

Subsequently, the same pair of stools was cut 33 days after the previous harvest for yield and nutritional analysis. The two stools had an average weight of 14.38 kilograms and an average stalk count of 180. Using the same extrapolation as above, the weight for one hectare at cutting computes to 63.90 metric tons/hectare (28.46 short tons/acre). The stools had an average height ranging from 1.20 to 1.30 meters and an average diameter ranging from 2.20 to 2.30 meters.

Nutritional analysis has been carried out on a number of the stools of the subject grass variety at various ages of harvest and the composite results, computed on a 100% dry basis, are as follows

| AGE | 2 WEEKS | 3 WEEKS | 4 WEEKS | 3 MONTHS |
|---|---|---|---|---|
| CRUDE PROTEIN | 31.71 | 23.91 | 19.11 | 15.52 |
| CRUDE FAT | 4.75 | 2.48 | 5.31 | 2.19 |
| ASH | 21.12 | 18.30 | 15.20 | 15.34 |
| CRUDE FIBER | 21.64 | 24.22 | 30.29 | 27.81 |
| NFE | 20.15 | 31.03 | 30.07 | 39.10 |
| ACID DETER. FIBER | 32.25 | — | — | — |
| CALC. TDN | 55.24 | 55.6 | 61.55 | 59.80 |

Coefficients from "Morrison's Feeds and Feeding for TDN." "TDN" stands for total digestible nutrients.

The exceptionally high protein content of the grass of the new variety permits its blending into a feed ration serving as a valuable source of amino acids. The grass has demonstrated salt tolerance and could become an economic crop for those areas in California with salt and alkali problems, such as the west side of the San Joaquin valley and in the Imperial valley. Replicated tests are currently being conducted to determine the degree of resistance to salt.

The grass of the subject variety can also be used for direct grazing by animals on a rotational basis and should be planted on a 1.0 by 1.0 meter, or 1.5 by 1.0 meter spacing to permit the animals to move about between the stools and not step on the grass. The height of the blade tips should initially be approximately 1.5 meters and the animals should be removed when they have grazed the blades to just above meristematic tissue. In this manner, the individual stools will rapidly grow new blades and permit the animals to reenter the pasture within the shortest possible time.

Two methods of commercial planting appear to be possible with this grass variety and systems and methods are being developed and projected at this time. A system has been studied to plant one eyed pre-germinated seed pieces which can be directly transplanted into a commercial field. Using this method, several thousand transplants have been grown using potting mixes and rooting and fungicidal chemicals and almost perfect germination was observed within 10 to 15 days of planting. Seed pieces are planted vertically with the buds up. Pre-germinated one eyed seed pieces could be planted in commercial areas approximately two to three weeks after germination and should be pruned to reduced evapo-transpiration. Initial studies employing a transplanting machine are being conducted for irrigated conditions. The transplanter would insert the pre-germinated seedling into the ground with adequate liquid fertilizer and starter solution and at the same time lay a subsurface irrigation system designed for soil type and plant consumptive use.

A second method of planting being developed is direct planting using culms with four to five buds and a machine similar to various sugarcane planters, such as the Cameco Billet Planter, or the Australian cut stalk planter. These devices would be modified structurally to carry rolls of irrigation tubing which would be installed thereby. Harvest methods for culms to be used for vegetative reproduction would use a machine similar to the Louisiana sugarcane Soldier Harvester. Such machines cut entire stalks and deposit them on the soil surface in bundles which are subsequently loaded into the planter or other transport by a use of self-propelled grab.

Harvesting equipment for the instant grass variety have been studied. Preliminary data indicates that common tpes of forage harvesters, either trailed or of the direct mounted self-propelled type, are entirely adequate for the subject grass variety. Larger field areas will be planted in the near future, which will be used to conduct variety tests for planting and harvesting combined with tests with animals.

Botanical Description Of The New Variety

Origin: Grass clone discovered in a cultivated field in a rural area near the city of Feira de Santana in the State of Bahia in Brazil growing with mixed clones of the species *Pennisetum purpureum.*

Stalk:

*Habit of growth.*—In plantings spaced on a square of 1.5 by 1.5 meters, the stool is erect with some of the individual stalks at the periphery inclining outward at angles varying in genral from 15° to 30°. Some of the weaker stalks, because of intense competition, can lodge on the ground. In plantings designed for harvesting by commercial, self propelled forage harvesters with row spacings of 0.80 to 1.0 meters and in-row spacings of 0.5 meters per stool, the individual stalks are more erect and almost no lodging occurs.

*Size.*—Depends on the age, order of branching and agronomic and climatic factors.

*Height.*—Forage — Generally harvested at one meter to one-and-one-half meters. Vegetative reproduction — Can attain heights of over five meters.

*Stools.*—A unique and identifying characteristic of the clone is its stooling (tillering) ability when compared to other varieties of elephant grass. Younger space planted stools exhibit over 150 individual culms. Competition forces a gradual reduction in culm numbers as the stool grows older. Plantings on a 0.80 meter row width at five months had stalk counts of up to 20 per stool. Because of competition in this type of planting, generally two stools are a normal population per lineal meter.

*Internodes.*—Length — Vary from 11.8 cm (4.72 inches) to 17.8 cm (7.12 inches) with an average of 14.5 cm (5.80 inches) according to the order of branching and to agronomic factors. Shape — Bobbin shaped. The cross section of the internode is elliptical with average measurements of 17.5 mm (0.7 inches) by 20.5 mm (0.82 inches) with the node averaging 25.5 mm (1.02 inches) by 30.8 mm (1.232 inches) in cross section.

*Bud groove.*—A very pronounced bud groove or furrow is present in all internodes and is observed from the base of the bud running vertically upward to the superior leaf scar. Width: Base — 8 mm (0.32 inches). Middle — 6 mm (0.24 inches). Point immediately below superior leaf scar — 5 mm (0.2 inches). Depth — Approximately 2 mm (0.08 inches).

*Tendency to crack.*—No growth cracks have been noted on the internodes of the stalk.

*Color.*—The stalk has a considerable amount of wax similar to sugar cane. The stalk color varies with a deeper greenish (Plate 23, 13 to 18) ring of varying height just below the leaf scar. This deeper greenish ring can be from 4 mm (0.16 inches) to 7 mm (0.28 inches) in average height. The ring is covered with wax as is the rest of the internode with the quantity of wax diminishing toward the growth ring and root band. The rest of the internode is a lighter greenish (Plate 17, F1 to F5) color. Wax is also present in the bud furrow.

*Growth ring.*—Height — Variable above the root band and around the circumference of the stalk. One side of the growth ring is slightly swollen, and this swollen side can reach 6 mm (0.24 inches) to 7 mm 0.28 inches) above the root band. The opposite side may be flush with the stalk and only 1 mm (0.04 inches) to 2 mm (0.08 inches) in height, or at times, higher. Color — Lighter (Plate 19, K5) than the stalk and appeard to be devoid of wax.

*Root band.*—Height — From 5 mm (0.2 inches) to 9 mm (0.36 inches) with concentric circles of root primordia. The lower circle of root primordia is more evident and pronounced with individual primordia a darker green or slightly brown at the tip of the protruding bulge or root cap when starting to germinate. The upper ring of root primordia is situated so that the upper caps are arranged obliquely to the bottom tire and are very pale green with a minute whitish circle around them (Plate 17, b-3). Leaf scar — Very evident and protrudes equally around the stalk.

Stem buds:

*General characteristics.*—The bud has a pointed, tall, deltoid shape and emanates from the superior part of the growth ring and quickly elongates above the growth ring in the second or third internode. The buds are initially flat, growing up the center of the bud furrow. As the buds mature, the protective tissue forming the deltoid shape tends to dry and fall off. The bud at this point is bulging and swollen.

*Width.*—From 2 mm (0.08 inches) to 4 mm (0.16 inches) at the bottom of the bud on the earliest internodes.

*Pubescence.*—Pubescence on the prophyll is evident on buds of the second and third internodes, but occurs mainly on the wings. This pubescence is classified as Group 4 as described in Artschwager and Brandes, "Sugarcane (*Saccharum officinarum* L)," in *Origin, Classification, Characteristics and Descriptions of Representative Clones USDA Agriculture Handbook,* 1958, pp. 122, 307.

*Bud.*—Length — Grows rapidly and can obtain lengths of 5 cm (2. inches) or more on the upper internodes. The buds can grow into lateral shoots in many instances and this shooting characteristic seems to be accelerated by agronomic conditions conducive to rapid growth.

Leaf:

*Blade.*—The upper blades are erect and give a semi-spiked appearance with the lower blades less rigid and bending downward in an arc. Length — Measurements of leaves 2 to 11 indicate that leaf length extends from 60.22 cm (24.08 inches) to 87.98 cm (35.192 inches) with an average of 83.98 cm (33.592 inches). Width — Measurements of the same leaves indicated a range of from 3.10 cm (1.24 inches) to 4.26 cm (1.704 inches) with an average of 3.83 cm (1.532 inches). The average length to width ratio is 21.78. Midrib — Very prominent and supports the leaf its entire length. Midrib — Color — The adaxial side is white and the abaxial side is green. Margin — The leaf has sharp serrated edge on both margins of the blade which can be seen in a 15 power lens. Pubescence — Evident on the blade and according to Artschwager's 1940 classification, Group 53 is present.

*Sheath.*—Length — Averages 18.88 cm (7.552 inches) and are tightly held to the stalk on the upper leaves. Only older leaves at the bottom of mature stalks when they are dried out and abscising are easily pulled off. Base — Flat with the base folded around itself and a triangular flap at the end of the fold.

*Dewlaps.*—According to Artschwager, "Structure And Taxonomic Valve Of The Dewl lap In Sugarcane," *USDA Technical Bulletin,* 1951, pp. 1038, 12, the dewlap is classified as a deltoid with downward sloping upper margins and baselines. Very prominent hair, or cilia, grow out of the point of attachment of the dewlap with the sheath.

*Ligule.*—There is no defined membrane. In place of the membrane there is a well defined hair group with an approximate length of 5 mm (0.2 inches) at the center of the midrib. Artschwager, "Morphology Of The Vegetative Organs Of Sugarcane J. Agriculture," 1940, Res., 60: 503–549, these hairs are classified as Groups 51 and 52. The hairs extend down to the base line and outer margin of the dewlap where they taper off to one millimeter or less.

Inflorescence:

*Panicle.*—Length — 15 cm (6 inches) to 30 cm (12 inches). Width — 2 cm (0.8 inches) to 4 cm (1.6 inches). Main axis — Straight to curved. Branch axis — (=peduncle ="pedicel" of involucre). Bristles — Antrorsely Scabrous @ terminal ~⅓ (=Distal ⅓). Retrorsely scabrous @ proximal ~⅔. Densely woolly, plumose, forming a fluffy ovate involucre.

*Spikelet.*—The spikelet is of a whitish coloration and contains up to 4 glumes. Length — 5 mm (0.2 inches) to 8 mm (0.32 inches). Width —Approximately one quarter the length.

Resistance to disease: No bacerial fungal, or viral diseases have been noted to attack the new variety either in plantings in Brazil, or in the United States.

Resistance to pests: No insect pests have been observed on the leaves or stalks in all of the locations in which the variety has been planted.

Although the new variety of grass possesses the described characteristics noted above as a result of the growing conditions prevailing near the city of Feira de Santana, State of Bahia, Brazil, as well as near Kingsburg in the central San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of elephant grass, what I claim as new and desire to be secured by Plant Letters Patent is:

1. A new and distinct variety of elephant grass substantially as illustrated and described which possesses the unique and distinctive characteristic, when compared with other varieties of elephant grass, of a stooling, or tillering, ability, and which produces exceptionally high yields with very high nutritional values, particularly of protein.

* * * * *

UNITED STATES PATENT AND TRADEMARK OFFICE

CERTIFICATE OF CORRECTION

PATENT NO. : PP 9,733

DATED : December 3, 1996

INVENTOR(S) : Morton S. Rothberg

It is certified that error appears in the above-identified patent and that said Letters Patent is hereby corrected as shown below:

Column 1, Line 41, the "p" in "purpureum" should be upper case.

Column 3, Line 18, delete "exhibied" and substitute ---exhibited---.

Column 3, Line 59, delete "ti" and substitute ---to---.

Column 6, Line 25, delete "tpes" and substitute ---types---.

Column 6, Line 36, the "p" in "purpureum" should be upper case.

Column 7, Line 35, delete "appeard" and substitute ---appears---.

Column 8, Line 34, delete "Dewl lap" and substitute ---Dewlap---.

Column 8, Line 55, the "s" in "scabrous" should be upper case.

Column 8, Line 61, delete "bacerial" and substitute ---bacterial---.

Signed and Sealed this

Twenty-fifth Day of February, 1997

*Attest:*

*Attesting Officer*

BRUCE LEHMAN

*Commissioner of Patents and Trademarks*